(12) United States Patent
Engel et al.

(10) Patent No.: US 6,992,206 B2
(45) Date of Patent: Jan. 31, 2006

(54) METHOD FOR PRODUCING 3-TRIFLUOROMETHYLPHENYL-4-CYANOBENZYL KETONE

(75) Inventors: Stefan Engel, Nieder-Olm (DE); Michael Keil, Freinsheim (DE); Christian Ott, Speyer (DE); Michael Rack, Heidelberg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/512,487

(22) PCT Filed: Apr. 25, 2003

(86) PCT No.: PCT/EP03/04327

§ 371 (c)(1),
(2), (4) Date: Oct. 26, 2004

(87) PCT Pub. No.: WO03/091203

PCT Pub. Date: Nov. 6, 2003

(65) Prior Publication Data

US 2005/0171373 A1 Aug. 4, 2005

(30) Foreign Application Priority Data

Apr. 26, 2002 (DE) .............................. 102 18 764

(51) Int. Cl.
*C07C 253/30* (2006.01)
(52) U.S. Cl. ............................................... 558/357
(58) Field of Classification Search ............... 558/357
See application file for complete search history.

(56) References Cited

FOREIGN PATENT DOCUMENTS

JP          4270248          9/1992

OTHER PUBLICATIONS

Derwent Abstract XP 002250631=JP 416826.
JP4270248=DW 92-369413.

*Primary Examiner*—Kamal A. Saeed
(74) *Attorney, Agent, or Firm*—Novak Druce & Quigg; Jason D. Voight

(57) ABSTRACT

A process is described for preparing 3-trifluoromethylphenyl 4-cyanobenzyl ketone by reacting a $C_1$–$C_2$-alkyl 3-trifluoromethylbenzoate with 4-tolunitrile in an aprotic polar solvent or an aprotic polar solvent mixture in the presence of at least an equimolar amount of a base which is selected from potassium alkoxides of primary $C_1$–$C_4$-alkanols.

7 Claims, No Drawings

METHOD FOR PRODUCING 3-TRIFLUOROMETHYLPHENYL-4-CYANOBENZYL KETONE

The present invention relates to a process for preparing 3-trifluoromethylphenyl 4-cyanobenzyl ketone.

α-Phenylacetophenones such as 3-trifluoromethylphenyl 4-cyanobenzyl ketone (also referred to as α-(4-cyanophenyl)-3-trifluoromethylacetophenone) is an important starting material for preparing crop protection agents (cf., for example, WO 00/18714).

JP 4168826 describes a process for preparing α-phenylacetophenones by condensing optionally substituted benzoic esters with substituted toluenes in the presence of at least equimolar amounts of base. The preparation of 3-trifluoromethylphenyl 4-cyanobenzyl ketone by reacting one equivalent of methyl 3-trifluoromethylbenzoate with one equivalent of 4-tolunitrile in N,N-dimethylformamide is described explicitly. Sodium hydride functions as the base. The process described is problematic from a safety standpoint, since reactions with sodium hydride in N,N-dimethylformamide may result in vigorous thermal decomposition reactions, cf. Chemistry & Engineering 1982, 5, July 12 and 1982, 43, September 13. Also, sodium hydride is self-igniting under damp air and reacts very vigorously with moisture to give hydrogen and sodium hydroxide solution. Therefore, the reactants and solvents used may have only an extremely low water content. However, the use of other bases such as sodium tert-butoxide leads to worse yields compared to sodium hydride, as can be seen from the examples 3 and 3-2 which describe the preparation of 3-chlorophenyl 4-cyanobenzyl ketone.

In-house investigations have also shown that of the other bases specified in JP 4168826, the use of potassium carbonate in N,N-dimethylformamide results in no reaction, and the use of sodium hydroxide in dimethyl sulfoxide results exclusively in hydrolysis of the ester to the corresponding acid as a by-product.

To avoid these problems, WO 00/18714 suggests converting such α-phenylacetophenones by reacting acetophenones with activated halobenzenes. A disadvantage of this is the moderate yield.

It is an object of the present invention to provide a technically safe, simple and economic process for preparing 3-trifluoromethylphenyl 4-cyanobenzyl ketone which allows high yields of product of value to be achieved.

We have found that this object is achieved, surprisingly, and that 3-trifluoromethylphenyl 4-cyanobenzyl ketone can be prepared in very good yield under technically safe and mild reaction conditions where a $C_1$–$C_2$-alkyl 3-trifluoromethylbenzoate is reacted with 4-tolunitrile in an aprotic polar solvent or an aprotic polar solvent mixture in the presence of at least equimolar amounts of potassium $C_1$–$C_4$-alkoxides of a primary $C_1$–$C_4$-alcohol.

The invention therefore relates to a process for preparing 3-trifluoromethylphenyl 4-cyanobenzyl ketone by reacting a $C_1$–$C_2$-alkyl 3-trifluoromethylbenzoate with 4-tolunitrile in an aprotic polar solvent or an aprotic polar solvent mixture in the presence of at least an equimolar amount of a base, wherein the base is selected from potassium alkoxides of primary $C_1$–$C_4$-alkanols.

The potassium alkoxides of primary $C_1$–$C_4$-alcohols include potassium methoxide, potassium ethoxide, potassium n-propoxide and potassium n-butoxide. Preference is given to potassium methoxide.

In general, the base is used in an at least equimolar amount, based on 4-tolunitrile. Preference is given to using from 1.1 to 5 equivalents of base, in particular from 1.5 to 4 equivalents, and most preferably from 2.01 to 3 equivalents, of base, based on 4-tolunitrile.

A preferred $C_1$–$C_2$-alkyl 3-trifluoromethylbenzoate is methyl 3-trifluoromethylbenzoate which is commercially obtainable. 4-Tolunitrile is likewise commercially obtainable.

According to the invention, the reaction medium is an aprotic polar solvent system which also includes mixtures of different aprotic, polar solvents and mixtures of aprotic, polar solvents with aprotic, nonpolar solvents. The proportion of nonpolar solvents will generally not exceed 50% by volume, in particular 20% by volume. The proportion of aprotic polar solvents in the solvent to be used according to the invention is therefore generally at least 50% by volume and preferably at least 80% by volume. The examples of aprotic, polar solvents include N,N-dimethylamides of aliphatic $C_1$–$C_4$-carboxylic acids such as N,N-dimethylformamide or N,N-dimethylacetamide, N-methyllactams such as N-methylpyrrolidone, dialkoxyalkanes such as 1,2-dimethoxyethane, diethylene glycol dialkyl ethers such as diethyl glycol dimethyl ether or diethyl glycol diethyl ether, sulfoxides such as dimethyl sulfoxide, sulfolane or tetraalkylureas such as tetramethylurea. In a preferred embodiment, at least one aprotic polar solvent is used as the sole reaction medium (>99% by volume, based on the entire solvent mixture) and is preferably selected from 1,2-dimethoxyethane, N,N-dimethylformamide and dimethyl sulfoxide, among which particular preference is given to N,N-dimethylformamide. Examples of preferred aprotic nonpolar solvents include aromatic hydrocarbons such as benzene, toluene or xylenes, cyclic hydrocarbons such as cyclohexane or aliphatic hydrocarbons such as n-heptane, n-hexane, isohexane (commercial hexane isomer mixture), decane and petroleum ether, although preference is given to aromatic hydrocarbons, in particular toluene and xylenes. In another preferred embodiment of the present invention, a solvent system is used which, in addition to the aprotic polar solvent, especially in addition to N,N-dimethylformamide, comprises from 1 to 50% by volume, preferably from 1 to 20% by volume and in particular from 2 to 15% by volume, of at least one aprotic nonpolar solvent, in particular at least one aromatic hydrocarbon and especially toluene and/or xylenes. Accordingly, the proportion of aprotic polar solvents in this mixture is from 50 to 99% by volume, preferably from 80 to 99% by volume and in particular from 85 to 98% by volume. The addition of nonpolar solvents as an additive to the aprotic polar solvents eases the technical handling of the reaction and leads in particular to a reduction in the viscosity of the reaction mixtures and in addition suppresses undesired fouling of tank walls and other apparatus parts such as stirrers and heat exchanger surfaces.

In general, the starting compounds 4-tolunitrile and $C_1$–$C_2$-alkyl 3-trifluoromethylbenzoate are reacted with each other in an equimolar ratio, although the ratio of the starting materials is of minor importance for the success of the reaction. However, a relatively large excess of 4-tolunitrile is generally avoided, since it can lead to the formation of undesired by-products. In general, the molar ratio of 4-tolunitrile to $C_1$–$C_2$-alkyl 3-trifluoromethylbenzoate will therefore generally not exceed a value of 2:1, in particular 1.5:1. However, it is also possible, conversely, to use the ester in excess, although this is generally avoided for reasons of cost. The molar ratio of 4-tolunitrile to trifluoromethylbenzoic ester will therefore preferably not fall below a value of 1:2 and in particular 1:1.5.

In a preferred embodiment, the molar ratio of the starting compounds 4-tolunitrile and $C_1$–$C_2$-alkyl 3-trifluoromethylbenzoate will be about 1:1, for example from 1.1:1 to 1:1.1.

The process according to the invention is generally performed at temperatures below 100° C., preferably not above 60° C., in particular in the range from +0 to 40° C.

The reaction pressure is of minor importance. Frequently, 4-tolunitrile is reacted with $C_1$–$C_2$-alkyl 3-trifluoromethylbenzoate in such a way that the solvent and the base are initially charged and the reactants are then added separately or as a mixture and optionally heated. When the reactants are added in succession, preference is given to initially adding the nitrile and then the ester. By its nature, the reaction time depends on the reaction temperature, reaction medium and base used and is generally in the range from 0.5 to 10 hours and in particular from 0.5 to 5 hours.

The reaction can be carried out by a batchwise or semi-batchwise method.

The reaction mixture is worked up and the product of value is removed by the customary techniques, for example by hydrolyzing the potassium enolate resulting from the reaction with aqueous acids such as hydrochloric acid, sulfuric acid or acetic acid, followed by an extractive workup. Any 3-trifluoromethylbenzoic acid formed as a by-product can be removed from the organic phase by alkaline extraction. The organic phase comprising the product of value may be used in subsequent reactions without further workup. Optionally, the solvent may also be removed to obtain the target compound in crystalline form.

The process according to the invention has a number of advantages over the process described in JP 4168826. Firstly, the dangerous use of sodium hydride in N,N-dimethylformamide can be dispensed with. Secondly, the organic phase comprising the product of value can be used in subsequent reactions immediately after the removal of the by-product formed, since the reaction mixture contains no interfering mineral oil from the sodium hydride. Also, the novel process is more economical, since relatively high yields of product of value are achieved even at relatively low reaction temperatures. However, when sodium tert-butoxide or potassium tert-butoxide are used as base, higher reaction temperatures are required and, in addition, the product of value is obtained in a worse yield.

The invention is illustrated by the examples which follow.

Preparation of 3-trifluoromethylphenyl 4-cyanobenzyl ketone.

EXAMPLE 1

In a reaction vessel, 10 equivalents of N,N-dimethylformamide were initially charged at 25° C. and 2.5 equivalents of potassium methoxide were added with stirring at this temperature. At this temperature, first 1 equivalent of methyl 3-trifluoromethylbenzoate and then 1 equivalent of 4-tolunitrile were then added. Reaction was allowed to proceed under the conditions specified in Table 1.

When the reaction mixture was heated to temperatures above 25° C., the reaction mixture was initially allowed to cool to temperatures below 40° C. Afterwards, the reaction mixture was admixed within 15 minutes with 3 equivalents of hydrochloric acid (10% by weight) and then with 25 equivalents of toluene. After extraction and phase separation, the organic extract was further extracted with 5% by weight aqueous sodium hydroxide solution. The yields of the title compound are reported in Table 1.

| Temperature [° C.] | Reaction time [h] | Yield [%] |
|---|---|---|
| 50 | 1.5 | 86 |
| 25 | 4.0 | 82 |
| 25 | 18.0 | 83 |

COMPARITIVE EXAMPLE 1

Example 1 was repeated, except that sodium methoxide was used instead of potassium methoxide. The reaction temperature was 25° C. and the reaction time was 25 hours. The title compound was obtained in a yield of 75%.

COMPARITIVE EXAMPLE 2

Example 1 was repeated, except that sodium tert-butoxide was used instead of potassium methoxide. After a reaction time of 2 hours at 80° C., the title compound was obtained in a 71% yield.

COMPARITIVE EXAMPLE 3

Example 1 was repeated, except that 2.1 equivalents of solid potassium tert-butoxide were used instead of 2.5 equivalents of potassium methoxide. After a reaction time of 6.5 hours at 50° C. under atmospheric pressure, the title compound was obtained in a 69.6% yield.

We claim:

1. A process for preparing 3-trifluoromethylphenyl 4-cyanobenzyl ketone by reacting a $C_1$–$C_2$-alkyl 3-trifluoromethylbenzoate with 4-tolunitrile in an aprotic polar solvent or an aprotic polar solvent mixture in the presence of at least an equimolar amount of a base, wherein the base is selected from potassium alkoxides of primary $C_1$–$C_4$-alkanol.

2. A process as claimed in claim 1, wherein from 2.01 to 3 equivalents of base are used, based on 4-tolunitrile.

3. A process as claimed in claim 1, wherein the aprotic polar solvent is selected from dimethylamides of aliphatic $C_1$–$C_4$-carboxylic acids, N-methyllactams, tetramethylurea, dialkoxyalkanes, diethyl glycol dialkyl ethers and dimethyl sulfoxide.

4. A process as claimed in claim 3, wherein the solvent is dimethylformamide.

5. A process as claimed in claim 1, wherein the aprotic polar solvent mixture comprises from 1 to 50% by volume of an aromatic hydrocarbon.

6. A process as claimed in claim 5, wherein the aprotic polar solvent mixture comprises dimethylformamide as the aprotic polar solvent and xylenes and/or toluene as the aromatic hydrocarbon.

7. A process as claimed in claim 1, wherein the reaction is carried out at a temperature in the range from 0 to 40° C.

* * * * *